US009298644B2

(12) United States Patent
Ryu et al.

(10) Patent No.: US 9,298,644 B2
(45) Date of Patent: Mar. 29, 2016

(54) METHOD AND PORTABLE DEVICE FOR MANAGING MEMORY IN A DATA STREAM MANAGEMENT SYSTEM USING PRIORITY INFORMATION

(75) Inventors: Seung-woo Ryu, Seoul (KR); Seok-jin Hong, Hwaseong-si (KR); Keun-joo Kwon, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 443 days.

(21) Appl. No.: 13/420,797

(22) Filed: Mar. 15, 2012

(65) Prior Publication Data

US 2012/0254575 A1 Oct. 4, 2012

(30) Foreign Application Priority Data

Mar. 28, 2011 (KR) ........................ 10-2011-0027559

(51) Int. Cl.
*G06F 13/00* (2006.01)
*G06F 12/12* (2006.01)
*G06F 12/08* (2006.01)
*G06F 19/00* (2011.01)

(52) U.S. Cl.
CPC .............. *G06F 12/121* (2013.01); *G06F 12/08* (2013.01); *G06F 12/123* (2013.01); *G06F 12/126* (2013.01); *G06F 19/3412* (2013.01)

(58) Field of Classification Search
CPC ... G06F 12/126; G06F 12/121; G06F 17/301; G06F 2209/5021; G06F 19/3412; G06F 12/08; G06F 12/123; G06F 17/30; Y02B 60/1225
USPC .......................................... 711/159, 133, 165
See application file for complete search history.

(56) References Cited

U.S. PATENT DOCUMENTS

| 5,944,815 | A * | 8/1999 | Witt ............................... 712/207 |
| 7,603,522 | B1 * | 10/2009 | Lepak et al. .................. 711/130 |
| 2002/0138699 | A1 * | 9/2002 | Okamura ....................... 711/133 |
| 2003/0088739 | A1 * | 5/2003 | Wilkes et al. ................. 711/133 |
| 2004/0193806 | A1 * | 9/2004 | Koga et al. .................... 711/133 |
| 2005/0031055 | A1 * | 2/2005 | Ernst ..................... H04L 25/068 375/342 |
| 2005/0208947 | A1 * | 9/2005 | Bahl .................... H04L 12/4633 455/450 |
| 2006/0026372 | A1 * | 2/2006 | Kim et al. ...................... 711/160 |
| 2008/0256046 | A1 * | 10/2008 | Blackman ......... G06F 17/30864 |
| 2009/0097623 | A1 * | 4/2009 | Bharadwaj .......... H04M 11/027 379/106.02 |
| 2009/0172315 | A1 * | 7/2009 | Iyer et al. ...................... 711/158 |
| 2009/0198790 | A1 * | 8/2009 | Grevers, Jr. ................... 709/213 |
| 2010/0080143 | A1 | 4/2010 | Topaltzas et al. |
| 2011/0035458 | A1 * | 2/2011 | Burnim ......................... 709/206 |
| 2011/0145505 | A1 * | 6/2011 | Anand et al. .................. 711/130 |
| 2011/0221595 | A1 * | 9/2011 | Koraichi .............. A61B 5/0002 340/573.1 |
| 2011/0320523 | A1 * | 12/2011 | Chan et al. .................... 709/203 |
| 2012/0054444 | A1 * | 3/2012 | Wang ............................ 711/133 |

(Continued)

FOREIGN PATENT DOCUMENTS

JP WO 2011010688 A1 * 1/2011 ......... H04N 7/17318
KR 10-2005-0096623 10/2005

(Continued)

*Primary Examiner* — Hong Kim
(74) *Attorney, Agent, or Firm* — NSIP Law

(57) ABSTRACT

Provided are method and device for managing a memory in a data stream management system (DSMS) of a portable device. The method includes moving data of a selected memory region that has a low priority to a secondary storage and storing a received data stream in the selected memory region.

20 Claims, 8 Drawing Sheets

(56) References Cited

U.S. PATENT DOCUMENTS

2012/0124159 A1* 5/2012 Takahashi ......... H04N 7/17318 709/213
2013/0144682 A1* 6/2013 Dhara .................... G06Q 10/04 705/7.29
2014/0089595 A1* 3/2014 Hyuseinova et al. ......... 711/134

FOREIGN PATENT DOCUMENTS

KR 10-2009-0120722 11/2009
KR 10-2010-0054014 5/2010

* cited by examiner

Queue

Operator

| Stream source | Periodic statistics | size | Last Time stamp |
|---|---|---|---|
| S1 | 10Min | 1MB | 100525 |
| S2 | 20Min | 5MB | 102030 |

| Sid | TIME UP TO NEXT STREAM | RECENT RECEIVING TIME |
|---|---|---|
| S2 | 10 | Last Time Stamp |
| S3 | 25 | Last Time Stamp |

| Sid | TIME UP TO NEXT STREAM | RECENT RECEIVING TIME |
|---|---|---|
| S2 | 2 | Last Time Stamp |
| S3 | 17 | Last Time Stamp |

METHOD AND PORTABLE DEVICE FOR MANAGING MEMORY IN A DATA STREAM MANAGEMENT SYSTEM USING PRIORITY INFORMATION

CROSS-REFERENCE TO RELATED APPLICATION(S)

This application claims the benefit under 35 U.S.C. §119 (a) of Korean Patent Application No. 10-2011-0027559, filed on Mar. 28, 2011, in the Korean Intellectual Property Office, the entire disclosure of which is incorporated herein by reference for all purposes.

BACKGROUND

1. Field

The following description relates to data processing, and more particularly, to memory management in a data stream management system (DSMS).

2. Description of the Related Art

Recent developments in the health care field make it possible to transmit information about a patient's state to a medical team from home or from a work place without the patient having to make a visit. This allows a patient to receive treatment remotely. A system for remotely providing a medical service is referred to as a connected healthcare system or a ubiquitous healthcare (U-healthcare) system.

For example, a U-healthcare system may measure electrical activity of a patient's heart using an electro-cardiogram (ECG) and transmit the results to a remote hospital in order to prevent and treat heart disease.

A U-healthcare system may collect medical information measured by a sensor that is attached to a human body, and may transmit data to a server of a hospital through a portable device. However, a portable device typically has a limited memory space, and thus, there is a need to manage a memory of the portable device to ensure that it is used effectively.

SUMMARY

In one general aspect, there is provided a method of managing a memory in a data stream management system (DSMS) of a portable device, the method including calculating values of a scoring function for a plurality of memory regions of a first memory area based on priorities of the plurality of memory regions, comparing the values of the scoring function of the plurality of memory regions and selecting a memory region that has a lowest priority, moving data of the selected memory region to a second memory area, and storing a received data stream in the selected memory region.

The calculating of the values of the scoring function for each memory region may comprise calculating the values of the scoring function by adding values together that are obtained by multiplying values of components that are to be considered by weights of the respective components.

The components used to calculate the value of each scoring function may comprise at least one of an expected time when at least one second data stream corresponding to a memory region is to be received, a data receiving state of a sensor for transmitting a second data stream to the portable device, a size of the corresponding memory region, and the number of second data streams corresponding to the memory region.

The method may further comprise determining a time when the second data stream is to be received next based on at least one of periodic information that is inserted into a line of syntax in order to generate the second data stream by a user of the DSMS, periodic information that is determined using times when the second data stream is received previously, and periodic information that is included as tag information in the second data stream, wherein the calculating of the value of the scoring function comprises lowering a priority of a memory region by increasing a weight, in response to a second data stream not being received during a predetermined amount of time.

The calculating of the value of the scoring function may comprise lowering a priority of a memory region by increasing a weight corresponding to a receiving state of data, in response to a second data stream not being received at an input expected time.

The calculating of the value of the scoring function may comprise lowering a priority of a memory region by increasing a weight corresponding to a size of the corresponding memory region, in response to a size of a memory to be used for calculation of the first data stream being similar to a size of the memory region.

The calculating of the value of the scoring function may comprise increasing a priority of a memory region by reducing a weight corresponding to the number, in response to the amount of second data streams to be received by the corresponding memory region increasing.

The memory region may comprise a synopsis which is a memory region corresponding to an operator of a data stream, or comprises a store which is a memory region shared by a plurality of operators.

In another aspect, there is provided a portable device for managing a memory in a data stream management system (DSMS), the portable device including a plurality of memory regions of a first memory area configured to store data streams, a calculator configured to calculate values of a scoring function for the plurality of memory regions based on the priorities of the plurality of memory regions, to compare the values of the scoring function of each of the memory regions to select a memory region that has a lowest priority, a second memory area configured to store data of the selected memory region, and a controller configured to move the data of the selected memory region to the second memory area.

The calculator may be configured to calculate the values of the scoring function for each memory region by adding values together that are obtained by multiplying values of components that are to be considered by weights of the respective components.

The components used to calculate the value of each scoring function may comprise at least one of an expected time when at least one second data stream corresponding to a memory region is to be received, a data receiving state of a sensor for transmitting a second data stream to the portable device, a size of the corresponding memory region, and the number of second data streams corresponding to the memory region.

The portable device may further comprise a stream periodic manager for determining a time when the second data stream is to be received next based on at least one of periodic information that is inserted into a line of syntax in order to generate the second data stream by a user of the DSMS, periodic information that is determined using times when the second data stream is received previously, and periodic information that is included as tag information in the second data stream, wherein the calculator is configured to lower a priority of a memory region by increasing a corresponding weight, in response to a second data stream not being received during a predetermined amount of time.

The calculator may be configured to lower a priority of a memory region by increasing a weight corresponding to a receiving state of data, in response to a second data stream not being received at an input expected time.

The calculator may be configured to lower a priority of a memory region by increasing a weight corresponding to a size of the corresponding memory region, in response to a size of a memory to be used for calculation of the first data stream being similar to a size of the memory region.

The calculator may be configured to increase a priority of a memory region by reducing a weight corresponding to the number.

The memory region may comprise a synopsis which is a memory region corresponding to an operator of a data stream, or comprises a store which is a memory region shared by a plurality of operators.

In another aspect, there is provided a computer-readable storage medium having stored therein program instructions to cause a processor to implement a method of managing a memory in a DSMS of a portable device, the method including calculating values of a scoring function for a plurality of memory regions of a first memory area based on priorities of the plurality of memory regions, comparing the values of the scoring function of the plurality of memory regions and selecting a memory region that has a lowest priority, moving data of the selected memory region to a second memory area, and storing a received data stream in the selected memory region.

Other features and aspects may be apparent from the following detailed description, the drawings, and the claims.

Figure 1:
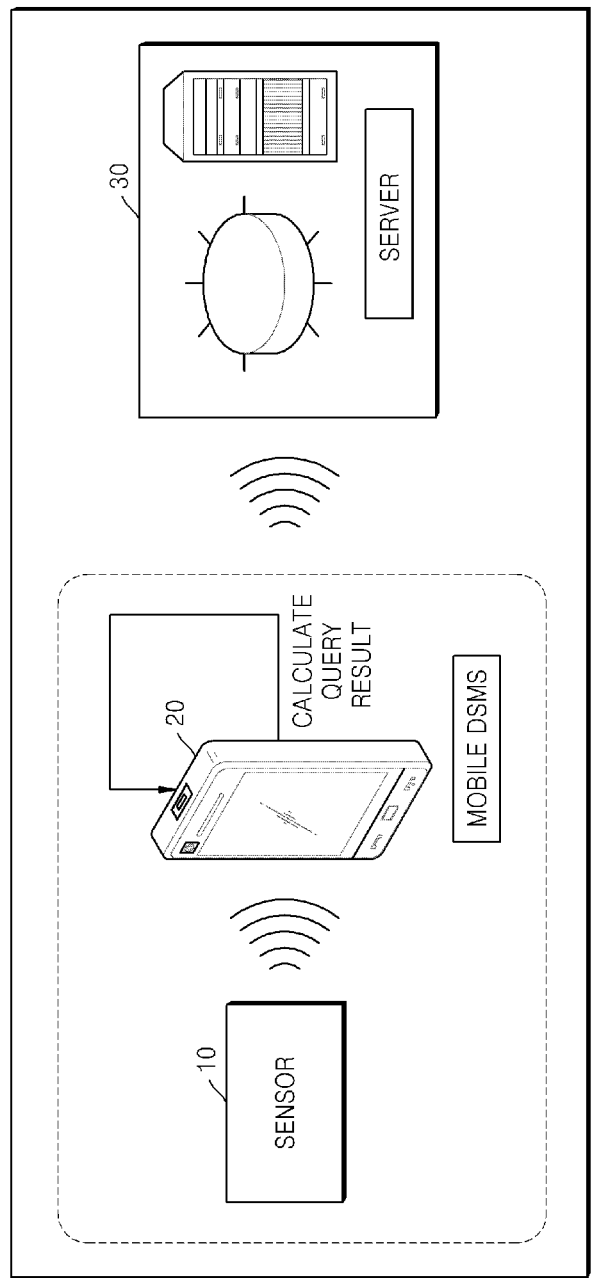
FIG. 1 is a diagram illustrating an example of a ubiquitous healthcare (U-healthcare) system.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

FIG. 1 illustrates an example of a ubiquitous healthcare (U-healthcare) system.

As shown in FIG. 1, a sensor 10 is attached to a patient's body in order to collect medical information. The medical information may be transmitted to a data stream management system (DSMS) of a server 30. However, it may be difficult for the sensor 10 to transmit data to a remote place. Accordingly, the sensor 10 may transmit the data to the server 30 through a portable device 20. For example, the portable device 20 may be a mobile terminal, a computer, a tablet, a smart phone, a medical device, and the like.

The portable device 20 may receive the data from the sensor 10 and transmit the data to the server 30. That is, the portable device 20 may function as a gateway.

In this example, the portable device 20 may also process the data as well as functioning as a gateway from the sensor 10 to the server 30. For example, the portable device 20 may include hardware that is capable of processing the data transmitted from the sensor 10. In some aspects, a mobile DSMS may be installed and operate in the portable device 20.

A power source may supply a smaller amount of power to the sensor 10 and/or the portable device 20 due to their limited sizes, in comparison to the server 30. Thus, a method of reducing power consumption may be used. In order to reduce power consumption, for example, the sensor 10 may use an ultra low power transmission system, a system for reconfigurable processor (SRP), and the like.

In order to reduce battery consumption of the sensor 10 and the portable device 20, various methods of reducing the amount of data transmitted may be used. For example, data may be compressed. That is, raw data extracted from the sensor 10 may be compressed.

As another example, periodic transmission may be used instead of real-time continuous transmission. The real time continuous transmission may be an optimal transmission method when a sufficient amount of power is supplied. However, in an example in which data is transmitted from the sensor 10 to the portable device 20, because the amount of data that is generated and transmitted is much smaller than a bandwidth used to transmit data, periodic transmission may be more effective than real-time continuous transmission, at least, from a battery power supply point of view. Typically, power consumed during data transmission is large, however, power consumption may be reduced when data is only transmitted for a short period of time with a high data rate in comparison to a case in which data is continually transmitted with a low data rate.

In an example in which real-time continuous transmission is not feasible due to a user's behavior patterns, periodic transmission may be performed. As another example, if a cellular phone functioning as a gateway is placed somewhere in order to charge the cellular phone, and a user moves to a different place in order to do other business, it may be difficult for a sensor to transmit data to the cellular phone. Therefore, data may be transmitted intermittently. A situation in which data is intermittently transmitted is referred to as an intermittence situation. In the intermittence situation, because it may be difficult to continually transmit data, a large amount of data may be transmitted using a periodic communication method or a non-periodic communication method.

In a mobile environment, a sensor may be installed directly in a portable device, or may be wired or wirelessly connected to the portable device through an ad-hoc network. In this case, in order to receive data from the sensor in a mobile DSMS on the portable device, the periodic transmission may be used to increase power efficiency. In an example in which a plurality of sensors are used, the sensors may have different receiving periods.

In a driving environment of a DSMS, it may be assumed that the DSMS operates in a server, and thus, a central processing unit (CPU) and a memory have sufficient capacities. In reality, in a system environment of a portable device, a system that has a very small size may be used in comparison to the size of the server. Compared to the server, a capacity of a memory of the portable device may be very small, and a memory space that is capable of being used by a user in reality, is further reduced. Thus, it may be assumed that the mobile DSMS has a different environment from the server, and the mobile DSMS may restrictively use a CPU and a memory.

As described in various example, the DSMS may have a different structure from a database management system (DBMS). For example, the DSMS may include a component for converting a data stream into a relation. In order to perform the conversion, a memory space may be assigned to an operator. Examples of the memory space may include a synopsis, a store, and the like. As described herein, a synopsis is a memory space for converting a data stream into a relation, and a single synopsis is assigned to and used in each operator. Synopses that have similar characteristics may be integrated with each other, and various operators may share the synopses as a memory space. In various examples, the memory space is referred to as a store.

Examples of the use of a memory region in a mobile DSMS are described with reference to FIGS. 2A through 4.

Figure 2A:
FIGS. 2A and 2B are diagrams illustrating examples of notations that are illustrated in FIGS. 3 and 4.
Figure 2B:
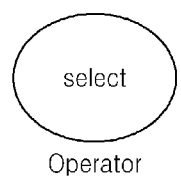
Figure 3:
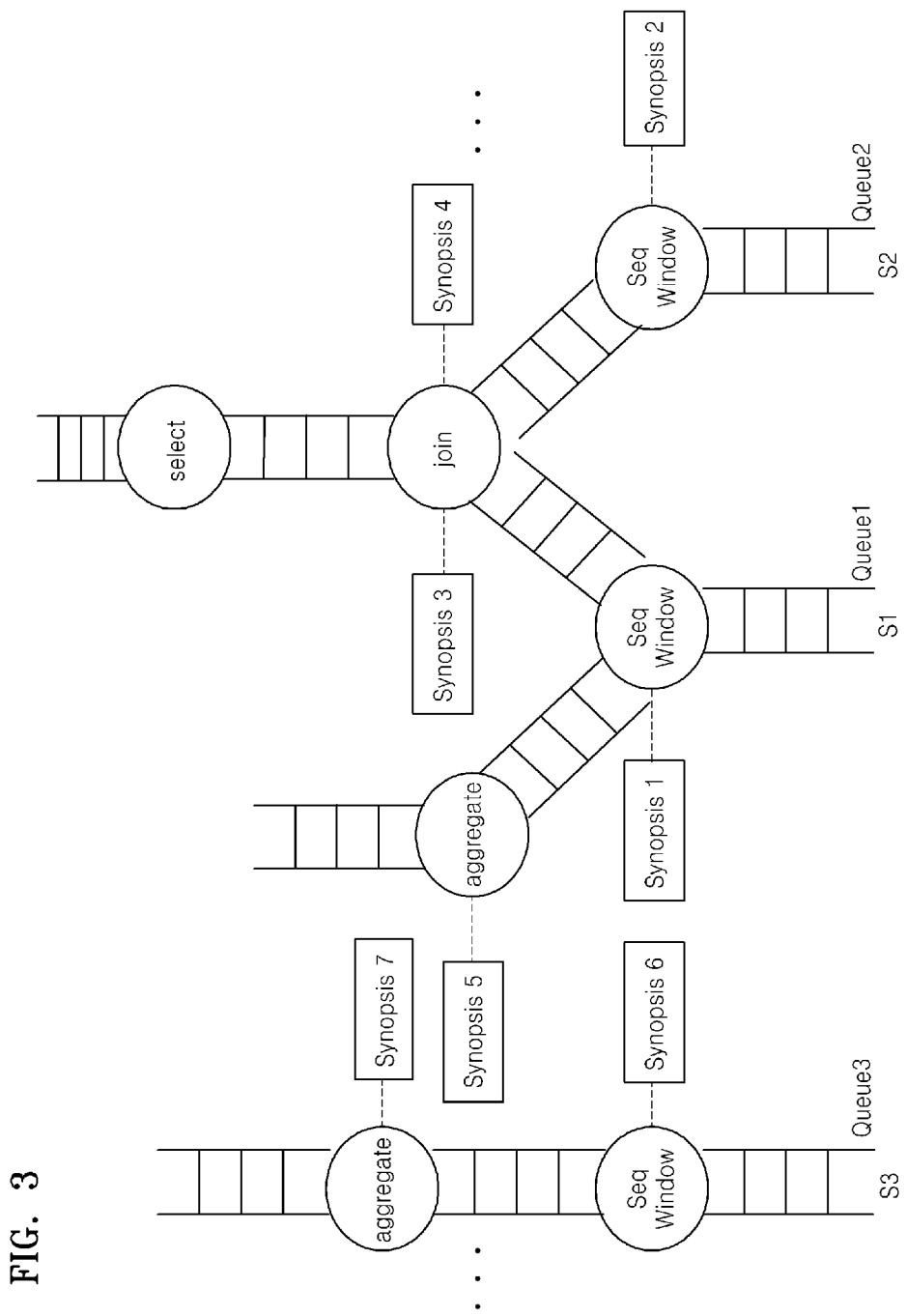
FIG. 3 is a diagram illustrating an example of a synopsis in a data stream management system (DSMS)
Figure 4:
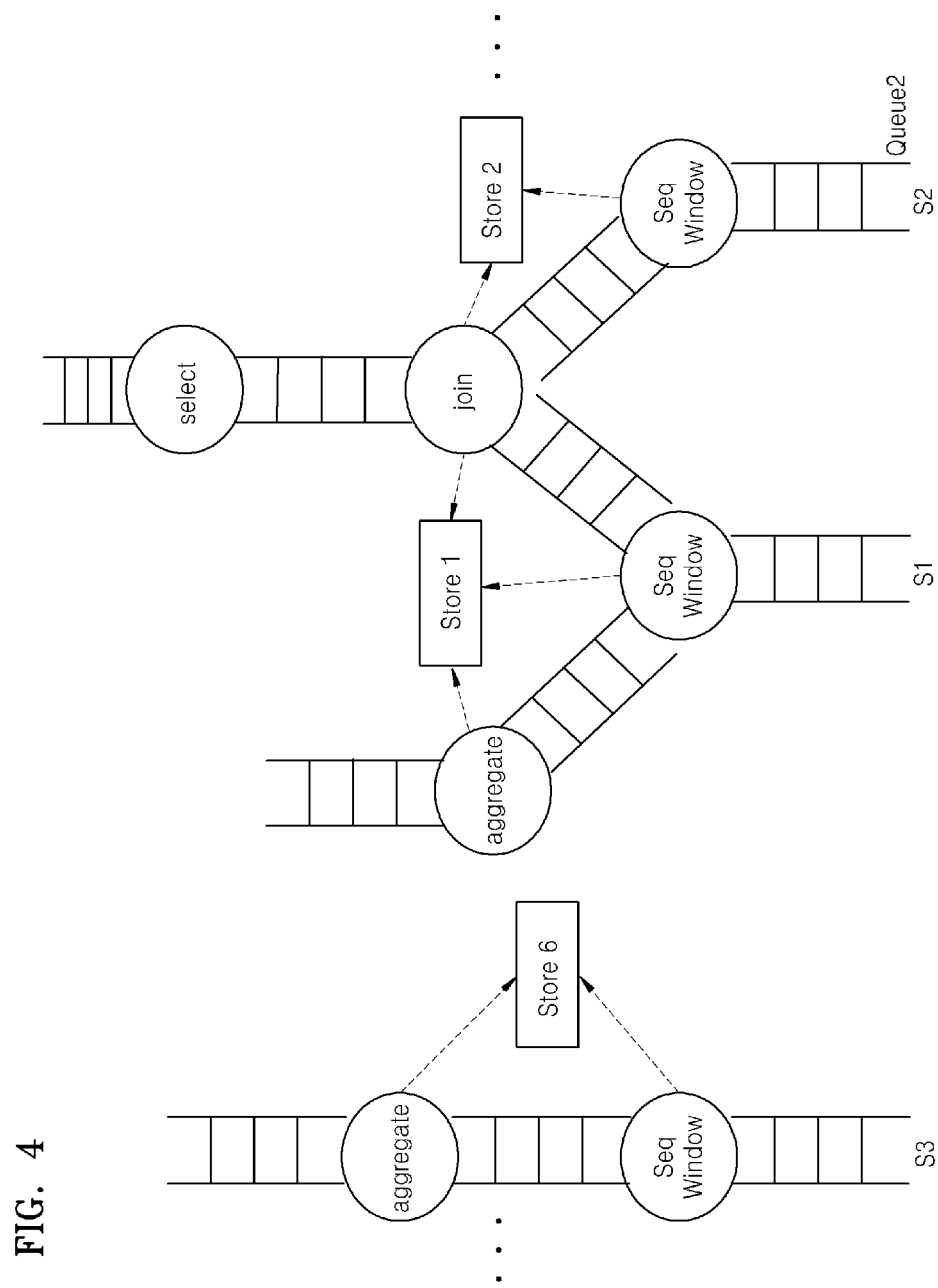
FIG. 4 is a diagram illustrating an example of a store in a DSMS.

FIGS. 2A and 2B illustrate examples of notations used in FIGS. 3 and 4. Referring to FIGS. 2A and 2B, a queue has a shape of a ladder, and an operator is configured by indicating a name of a corresponding operator in a circle. FIG. 2B illustrates an example of a select operator.

The mobile DSMS may receive a plurality of data streams using various applications, and a plurality of queries may be used for the respective applications.

Hereinafter, it is assumed that the following three queries are used.

Istream (Select sum($f3$) From $S3$ [Row 100])            Query 1

Istream (Select count(*) From $S1$ [Row 100] Where $S1.f1 > 50$)            Query 2

Istream (Select $S1.f1$, $S2.f2$ From $S1$ [Row 100], $S2$ [Range 1 Min] Where $S1.f1 = S2.f1$)            [Query 3]

A memory environment shown in FIG. 3 or 4 may be generated according to Queries 1, 2 and 3. This structure of the memory is referred to as a physical plan.

FIG. 3 illustrates an example of a synopsis in a DSMS.

Referring to FIG. 3, a data stream S1 corresponds to Queue 1, a data stream S2 corresponds to Queue 2, and a data stream S3 corresponds to Queue 3.

According to Query 1, a calculation for obtaining a sum is performed on 100 rows 'Row 100' of the data stream S3. Thus, an operator 'Seq Window' for checking the 100 rows 'Row 100', and an operator 'aggregate' corresponding to the sum are generated. Synopses are assigned to the respective operators. In this example, a synopsis 6 is assigned to the operator 'Seq Window', and a synopsis 7 is assigned to the operator 'aggregate'.

According to Query 2, a count calculation for counting the number of cases in which a value of S1.f1 is greater than 50 is performed on the 100 rows 'Row 100' of the data stream S1. In this example, a synopsis 1 is assigned to the operator 'Seq Window' for checking the 100 rows 'Row 100', and a synopsis 5 is assigned to the operator 'aggregate' corresponding to the count calculation for counting the number of cases.

According to Query 3, a select calculation for selecting data of which S1.f1 is equal to S2.f1 is performed on the 100 rows 'Row 100' and data for 1 minute 'Range 1 Min' of the data stream S2. In this example, a synopsis 2 is assigned to the operator 'Seq Window' for checking the data for 1 minute 'Range 1 Min' of the data stream S2, and synopses 3 and 4 are assigned to an operator 'Join' for combining two data streams in order to compare S1.f1 and S2.f2.

As shown in the example of FIG. 3, a single synopsis may be assigned to a single operator (e.g., the synopses 1, 2, 5, 6, and 7), and a plurality of synopses may be assigned to a single operator (e.g., the synopses 3, and 4).

The synopses 1, 3, and 5 are regions for storing data of data stream S1, and are similar to each other. The synopses 2 and 4 are regions for storing data of the data stream S2, and are similar to each other. The synopses 6 and 7 are regions for storing data of the data stream S3, and are similar to each other.

In this example, similar synopses may be integrated into a single memory region, and may be assigned to a store.

FIG. 4 illustrates an example of a store in a DSMS.

Referring to FIGS. 3 and 4, the synopses 1, 3, and 5 (shown in FIG. 3) are integrated with each other and are assigned to a store 1, the synopses 2 and 4 are integrated with each other and are assigned to a store 2, and the synopses 6 and 7 are integrated with each other and are assigned to a store 6.

Typically in a server a sufficient memory space is provided thus, the server typically has a memory space sufficient to be occupied by the above-described synopses or stores. That is, when a synopsis or a store is assigned, it is possible for the synopsis or the store to occupy a corresponding memory region in a server until all calculations are completely performed according to queries.

On the other hand, typically a sufficient memory space is not provided in a DSMS of a portable device. Thus, if a synopsis or a store occupies a corresponding memory region until all calculations are completely performed according to queries, there may be a shortage of memory in the DSMS.

Figure 5:
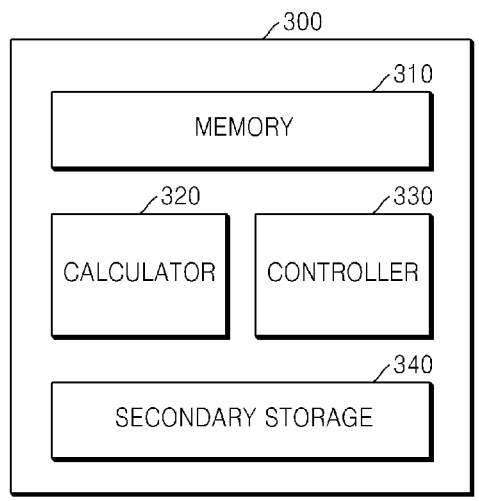
FIG. 5 is a diagram illustrating an example of a portable device.

FIG. 5 illustrates an example of a portable device.

Referring to FIG. 5, portable device 300 includes a memory 310, a calculator 320, a controller 330, and a secondary storage 340.

The memory 310 includes a plurality of memory regions for storing data. For example, the memory regions may each be a synopsis or a store. The memory 310 may also be referred to as a first memory area.

The calculator 320 may calculate functions of a scoring function with respect to respective memory regions. The scoring function is a number that represents a priority of data stored in a corresponding memory region. For example, if a priority of a memory region is lower, the scoring function may be set to a greater value. In this example, a memory region (hereinafter, referred to as a 'victim') that has the greatest value for the scoring function may be moved to the secondary storage 340.

The controller 330 may compare values of the scoring function of the memory regions, and move data of a memory region that has a lowest priority to the secondary storage 340.

In this example, the secondary storage 340 is a storage device for storing data of a memory region that has a low priority. For example, the secondary storage 340 may be a magnetic disk, an optical disk, a flash disk, and the like. The secondary storage 340 may also be referred to as a second storage area.

In the example of FIG. 3, the memory region 310 and the secondary storage 340 are illustrated as two separate storage areas that are included in the portable device 300. In the alternative, the memory region 310 and the secondary storage 340 may be included in the same storage area of a device such as the portable device 300. As another example, the memory region 310 may included in a storage area of a first device such as the portable device 300, and the secondary storage 340 may be included in a storage area of a second device (not shown).

Figure 6:
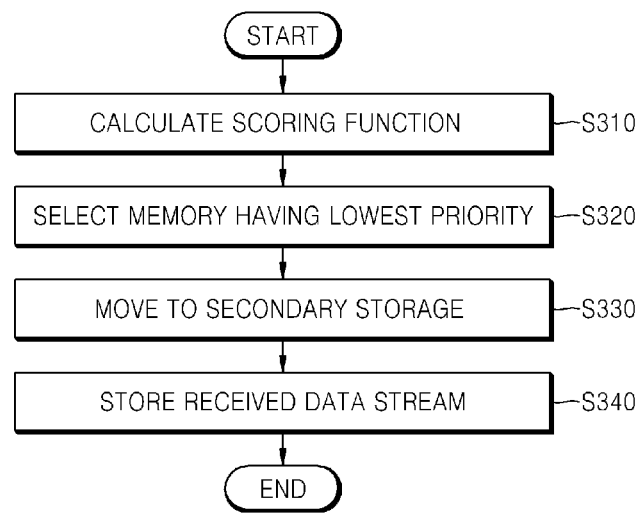
FIG. 6 is a flowchart illustrating an example of a method of managing a memory.

FIG. 6 illustrates an example of a method of managing a memory, according to an embodiment of the present invention.

Referring to FIG. 6, values of the scoring function are calculated according to a priority of memory regions in a DSMS of a portable device (S310). The values of the scoring function are compared to determine a memory region that has the lowest priority (S320). Data of the selected memory region is moved to a secondary storage (S330), and a received data stream is stored in the selected memory region (S340).

As described herein, to effectively use a memory region occupied by a synopsis or a store, values of the scoring function may be calculated, a synopsis or store with the lowest priority may be selected as a victim from among synopses or stores, and contents of the synopsis or store that are selected as the victim, that is, data of a corresponding memory region, may be moved to a storage (i.e., a secondary storage). When the data of the corresponding memory region, which is stored in the secondary storage, is needed again, the data may be moved back to a memory (which is referred to as 'load').

There are various components that may be considered in order to calculate values of the scoring function. Examples of the component may include a time (hereinafter, referred to as an input expected time) when a data stream corresponding to a corresponding memory region is to be received next, a connection and receiving state of a sensor, a size of a corresponding memory region (a synopsis or a store), the number of cases in which the corresponding memory region is shared by data streams (in the case of a store), and the like.

In order to calculate functions of the scoring function, values may be obtained by multiplying values of the components with weights of the respective components, and added together. For example, with regard to components A and B, the values of the scoring function may be calculated according to Scoring function=A*(weight of A)+B*(weight of B).

As an example, if the input expected time of a next data stream is considered, the input expected time may be obtained based on a current time using a receiving period of a data stream.

As another example, if the connection and receiving state of the sensor are considered, if a data stream is not received after the receiving period elapses, the connection and receiving state of the sensor may be determined as an intermittence situation. When the intermittence situation occurs, a method of setting a different weight may be used. For example, if a data stream is not received for the first time after the receiving period elapses, a weight may be small. However, if a data stream is not received again after the receiving period elapses, the weight may be doubled or more. In this example, because a weight is increased each time a data stream is not received for the first time after the receiving period elapses, a chance that a corresponding memory region is a victim is increased.

As another example, a size of a synopsis or store may be considered in order to select a memory region that has a size that is as similar as possible to a more necessary memory space.

As another example, if the number of cases in which a store is shared by data streams is considered, a store that is shared by data streams many times may be set to have a low weight so that a chance that the store is a victim may be lowered. If the store is shared by data streams many times, an input data stream is likely to be closely related to the store. Thus, if the store is moved to a secondary storage, the store will likely be needed again within a short period of time, so the store may be loaded to a memory.

The size and sharing number of a store may be registered as a point of time when a query is registered, that is, a register query calculation may be performed.

Other examples of components to be considered may include parameters required in a synopsis or store.

Figure 7:
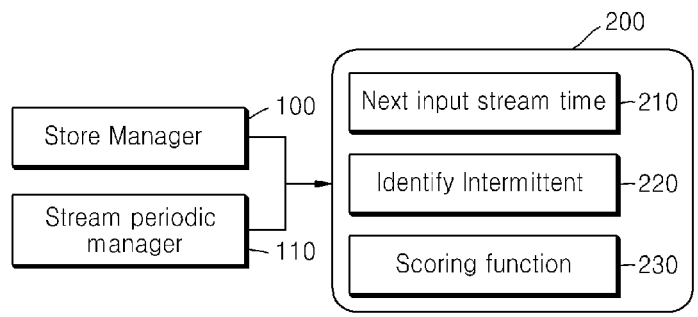
FIG. 7 is a diagram illustrating an example of managers for managing components.

FIG. 7 illustrates an example of managers for considering and managing components.

Referring to FIG. 7, a store manager 100 may manage the size and sharing number of a store. A stream periodic manager 110 may manage a receiving period of a stream. A victim manager 200 corresponds to the calculator 320 shown in FIG. 5. In this example, the victim manager 200 includes a unit 210 for managing a next input stream time, a unit 220 for identifying an intermittence situation, and a unit 230 for calculating a scoring function.

Figure 8:
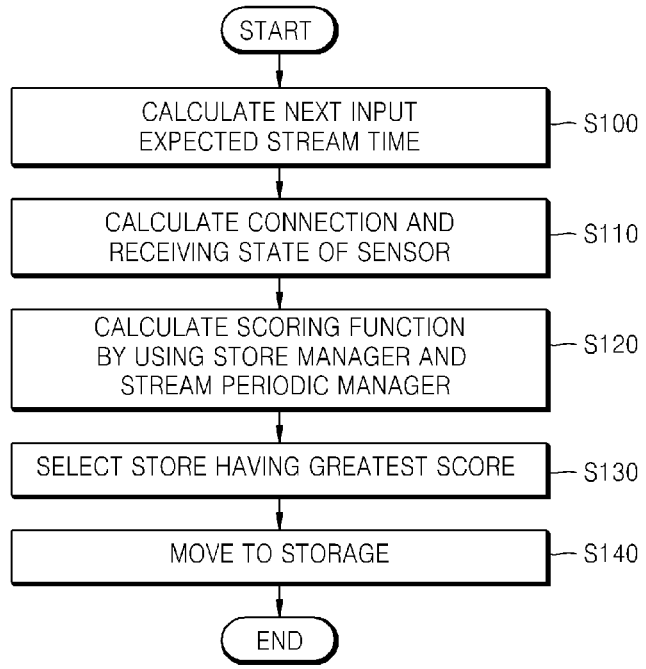
FIG. 8 is a flowchart illustrating another example of a method of managing a memory.

FIG. 8 illustrates another example of a method of managing a memory.

Referring to FIGS. 7 and 8, the unit 210 for managing a next input stream time receives information about a receiving period from the stream periodic manager 110, and determines a next input expected time based on a current time (S100).

The unit 220 for identifying an intermittence situation calculates a connection and receiving state of a sensor (S110).

The victim manager 200 receives information about components from the store manager 100 and the stream periodic manager 110, and calculates the scoring function based on the information about components (S120).

The victim manager 200 selects a memory region (a synopsis or a store) that has a scoring function with the greatest value (S130).

Data of the selected memory region is moved to a secondary storage (S140).

Examples of a method of obtaining a period of a stream include the following methods.

1. In a first method, a period of a stream is obtained by inserting periodic information into a line of syntax 'CREATE STREAM' for generating a data stream.

An example of the line of syntax is as follows.

CREATE STREAM S1 (sid, value, timestamp) PERIOD 1 hour

2. In a second method, a period of a stream is obtained based on an input value of the stream. That is, periodic information is determined using times when data streams are received previously.

In this example, a value of the last time when a stream is received, and a value of a time when a stream is currently received may be stored in a memory, and may be compared. A period may be obtained using a statistical inference method, for example, a method of calculating an average value, and the like. As an example, when the statistical inference method is used, information that a period of a stream S1 is an average 11 minutes, and a period of a stream S2 is an average 15 minutes may be calculated.

3. A third method is a method of using tag information in a stream or using stream notification using a predetermined signal.

In response to tag information being received, a receiving period may be obtained by recording a time contained in the tag information, obtaining a previous receiving time, and comparing the time and the previous receiving time. For example, the tag information may be different from original stream information, and may include a current time, sid, and the like. When a sensor transmits streams, the sensor may add the tag information to a bundle of the streams.

Examples of a method of managing a period of a stream include the following methods.

1. A first method is a method of adding periodic information to a line of syntax.

Figures 9A, 9B:
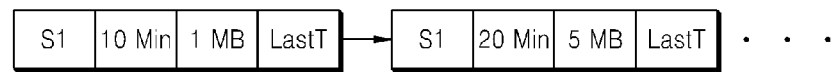
FIG. 9A is a table illustrating an example of periodic information that is stored in the form of a table.
FIG. 9B is a diagram illustrating an example of periodic information that is stored in the form of a linked list.

The stream periodic manager 110 may manage the periodic information in the form of a table. FIG. 9A illustrates an example of periodic information that is stored in the form of a table.

In addition, the periodic information may be managed in the form of a linked-list according to a periodic order. FIG. 9B illustrates an example of periodic information that is stored in the form of a linked list.

2. A second method is a method of managing an obtained receiving period of a stream.

A receiving period may be obtained based on a previous stream and a current stream, and then may be managed in the form of table or in the form of an ordered linked-list in a memory.

An input expected time of a next stream may be obtained as follows. The input expected time may be calculated during the selection of a victim.

Figures 10A, 10B, 11:
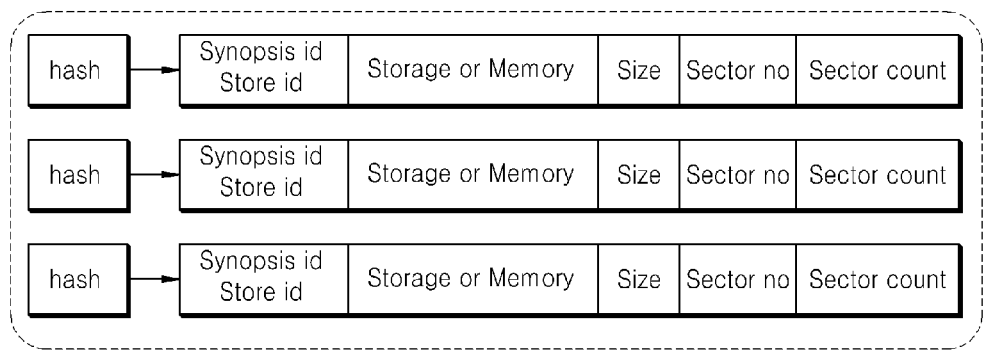
FIG. 10A is a table illustrating an example of previous periodic information when a first victim is selected.
FIG. 10B is a table illustrating an example of an input expected time of a stream after the table in a memory is updated based on a current time.
FIG. 11 is a diagram illustrating an example of managing a synopsis identification (ID) or a store ID in a store manager.

FIG. 10A is a table that illustrates previous periodic information when a first victim is selected. In this example, when 8 minutes elapse in a state shown in FIG. 10A, and the table is updated based on a current time, a period of time up to a next stream, that is, an input expected time, may be calculated as shown in FIG. 10B.

The input expected time may be input as a component that is considered when the scoring function is calculated.

When the connection and receiving state of the sensor are considered, the input expected time may be calculated during selection of a victim. Based on 'Last Time Stamp' (a time when a recent stream is input), a receiving state of a current stream may be obtained with reference to periodic information. In addition, it may be determined how long an intermittence situation is maintained.

For example, if a difference between a current time and a time when a previous stream is input largely exceeds a receiving period, a current situation may be determined as the intermittence situation.

Current Time-period>>Last Time Stamp

If the intermittence situation is maintained, priority of a corresponding memory region may be lowered by increasing a weight of the memory region. With regard to a data stream that is not received for a long time, because the intermittence situation is likely to be maintained, the data stream may be moved to a secondary storage and a serious problem is not likely to arise.

FIG. 11 illustrates an example a method of managing a synopsis ID or a store ID in a store manager.

In response to a physical plan being generated, the store manager 100 may generate the synopsis ID or the store ID. In this example, the synopsis ID and the store ID are managed by the store manager 100. In order to manage the synopsis ID and the store ID, a material structure such as a hash or a linked list may be used.

The hash may be used to manage all IDs used in an operator, and may be used to indicate whether data of a synopsis or store is stored in a storage or exists in a memory.

If the data is stored in the storage, a size of byte unit, a sector number (sector no.), and a sector count may be recorded.

When a synopsis or a store is selected as a victim, an ID corresponding to the synopsis or the store may be searched for in a hash structure, and whether data of the synopsis or store is stored in a storage or exists in a memory, a size of byte unit, a sector number (no.), and a sector count may be written.

It should be appreciated that a method of managing a memory according to various examples is not limited to a synopsis or a store, and may be used in all fields using a mobile DSMS.

As described herein, by managing a memory of a portable device, a memory region such as a synopsis, a store, or the like may be effectively used in a mobile DSMS that has a limited memory. In the mobile DSMS that has a limited memory, a memory region that is used a lowest number of times may be selected based on a scoring function using a periodic receiving attribute of a stream, and data of the memory region may be moved to a secondary storage, thereby obtaining an additional memory space for data that is more likely to be used.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable storage mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

As a non-exhaustive illustration only, a terminal/device/unit described herein may refer to mobile devices such as a cellular phone, a personal digital assistant (PDA), a digital camera, a portable game console, and an MP3 player, a portable/personal multimedia player (PMP), a handheld e-book, a portable lab-top PC, a global positioning system (GPS) navigation, a tablet, a sensor, and devices such as a desktop PC, a high definition television (HDTV), an optical disc player, a setup box, a home appliance, and the like that are capable of wireless communication or network communication consistent with that which is disclosed herein.

A computing system or a computer may include a microprocessor that is electrically connected with a bus, a user interface, and a memory controller. It may further include a flash memory device. The flash memory device may store N-bit data via the memory controller. The N-bit data is processed or will be processed by the microprocessor and N may be 1 or an integer greater than 1. Where the computing system or computer is a mobile apparatus, a battery may be additionally provided to supply operation voltage of the computing system or computer. It will be apparent to those of ordinary skill in the art that the computing system or computer may further include an application chipset, a camera image processor (CIS), a mobile Dynamic Random Access Memory (DRAM), and the like. The memory controller and the flash memory device may constitute a solid state drive/disk (SSD) that uses a non-volatile memory to store data.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of managing a memory in a data stream management system (DSMS) of a portable device, the method comprising:
    calculating values of a scoring function using an expected receiving periodicity of received data streams for memory regions of a first memory area, according to priorities of the memory regions;
    comparing the values of the scoring function of the memory regions and selecting a memory region that has a lowest priority;
    moving data of the selected memory region to a second memory area; and
    storing the received data stream in the selected memory region.

2. The method of claim 1, wherein the calculating of the values of the scoring function for each memory region comprises calculating the values of the scoring function by adding values together that are obtained by multiplying values of components that are to be considered by weights of the respective components.

3. The method of claim 2, wherein the components used to calculate the value of each scoring function comprise at least one of an expected time when at least one second data stream corresponding to a memory region is to be received, a data receiving state of a sensor for transmitting a second data stream to the portable device, a size of the corresponding memory region, and the number of second data streams corresponding to the memory region.

4. The method of claim 3, further comprising determining a time when the second data stream is to be received next based on at least one of periodic information that is inserted into a line of syntax in order to generate the second data stream by a user of the DSMS, periodic information that is determined using times when the second data stream is received previously, and periodic information that is included as tag information in the second data stream,
    wherein the calculating of the value of the scoring function comprises lowering a priority of a memory region by increasing a weight, in response to a second data stream not being received during a predetermined amount of time.

5. The method of claim 3, wherein the calculating of the value of the scoring function comprises lowering a priority of a memory region by increasing a weight corresponding to a receiving state of data, in response to a second data stream not being received at an input expected time.

6. The method of claim 3, wherein the calculating of the value of the scoring function comprises lowering a priority of a memory region by increasing a weight corresponding to a size of the corresponding memory region, in response to a size of a memory to be used for calculation of the first data stream being similar to a size of the memory region.

7. The method of claim 3, wherein the calculating of the value of the scoring function comprises increasing a priority of a memory region by reducing a weight corresponding to the number, in response to the amount of second data streams to be received by the corresponding memory region increasing.

8. The method of claim 1, wherein the memory region comprises a synopsis which is a memory region corresponding to an operator of a data stream, or comprises a store which is a memory region shared by operators.

9. A portable device for managing a memory in a data stream management system (DSMS), the portable device comprising:
    memory regions of a first memory area configured to store data streams;
    a calculator configured to calculate values of a scoring function using expected receiving periodicity of the received data streams for memory regions, according to the priorities of the memory regions, to compare the values of the scoring function of each of the memory regions to select a memory region that has a lowest priority;
    a second memory area configured to store data of the selected memory region; and
    a controller configured to move the data of the selected memory region to the second memory area.

10. The portable device of claim 9, wherein the calculator is configured to calculate the values of the scoring function for each memory region by adding values together that are obtained by multiplying values of components that are to be considered by weights of the respective components.

11. The portable device of claim 10, wherein the components used to calculate the value of each scoring function comprise at least one of an expected time when at least one second data stream corresponding to a memory region is to be received, a data receiving state of a sensor for transmitting a second data stream to the portable device, a size of the corresponding memory region, and the number of second data streams corresponding to the memory region.

12. The portable device of claim 11, further comprising a stream periodic manager for determining a time when the second data stream is to be received next based on at least one of periodic information that is inserted into a line of syntax in order to generate the second data stream by a user of the DSMS, periodic information that is determined using times when the second data stream is received previously, and periodic information that is included as tag information in the second data stream,
    wherein the calculator is configured to lower a priority of a memory region by increasing a corresponding weight, in response to a second data stream not being received during a predetermined amount of time.

13. The portable device of claim 11, wherein the calculator is configured to lower a priority of a memory region by increasing a weight corresponding to a receiving state of data, in response to a second data stream not being received at an input expected time.

14. The portable device of claim 11, wherein the calculator is configured to lower a priority of a memory region by increasing a weight corresponding to a size of the corresponding memory region, in response to a size of a memory to be used for calculation of the first data stream being similar to a size of the memory region.

15. The portable device of claim 11, wherein the calculator is configured to increase a priority of a memory region by reducing a weight corresponding to the number.

16. The portable device of claim 9, wherein the memory region comprises a synopsis which is a memory region corresponding to an operator of a data stream, or comprises a store which is a memory region shared by operators.

17. A non-transitory computer-readable storage medium having stored therein program instructions to cause a processor to implement a method of managing a memory in a DSMS of a portable device, the method comprising:
calculating values of a scoring function using expected receiving periodicity of received data streams for memory regions of a first memory area, according to priorities of the memory regions;
comparing the values of the scoring function of the memory regions and selecting a memory region that has a lowest priority;
moving data of the selected memory region to a second memory area; and
storing the received data stream in the selected memory region.

18. The method of claim 1, further comprising establishing a sensor remotely disposed from the management system (DSMS) to collect sensed data and transmit said sensed data to the DSMS at a predefined transmission periodicity.

19. The method of claim 18, further comprising, establishing the expected receiving periodicity of a received data stream according to the transmission periodicity.

20. The portable device of claim 9, further comprising a sensor coupled to a patient's body configured to collect medical information, the sensor being communicatively coupled to the memory regions with a transmission periodicity; and,
the calculator being further configured to calculate values of a scoring function using expected receiving periodicity based on the transmission periodicity of the sensor.

* * * * *